(12) United States Patent
Reiley

(10) Patent No.: US 9,861,404 B2
(45) Date of Patent: Jan. 9, 2018

(54) DEVICES, SYSTEMS AND METHODS FOR RE-ALIGNMENT OF BONE

(71) Applicant: Inbone Technologies, Inc., Berkeley, CA (US)

(72) Inventor: Mark A. Reiley, Piedmont, CA (US)

(73) Assignee: INBONE TECHNOLOGIES, INC., Berkeley, CA (US)

(*) Notice: Subject to any disclaimer, the term of this patent is extended or adjusted under 35 U.S.C. 154(b) by 0 days.

(21) Appl. No.: 14/615,137

(22) Filed: Feb. 5, 2015

(65) Prior Publication Data

US 2015/0164564 A1 Jun. 18, 2015

Related U.S. Application Data

(60) Continuation of application No. 13/747,031, filed on Jan. 22, 2013, now abandoned, which is a division of application No. 12/006,720, filed on Jan. 4, 2008, now abandoned.

(51) Int. Cl.
| | | |
|---|---|---|
| *A61B 17/80* | (2006.01) | |
| *A61B 17/84* | (2006.01) | |
| *A61B 17/56* | (2006.01) | |
| *A61B 17/68* | (2006.01) | |

(52) U.S. Cl.
CPC .......... *A61B 17/80* (2013.01); *A61B 17/8095* (2013.01); *A61B 17/846* (2013.01); *A61B 2017/564* (2013.01); *A61B 2017/681* (2013.01)

(58) Field of Classification Search
CPC ................................................. A61B 17/8095
See application file for complete search history.

(56) References Cited

U.S. PATENT DOCUMENTS

| | | | |
|---|---|---|---|
| 4,347,234 A | | 8/1982 | Wahlig et al. |
| 4,421,112 A | | 12/1983 | Mains et al. |
| 5,053,039 A | | 10/1991 | Hofmann et al. |
| 5,569,250 A | | 10/1996 | Sarver et al. |
| 5,620,448 A | | 4/1997 | Puddu |
| 5,749,875 A | | 5/1998 | Puddu |
| 5,766,251 A | | 6/1998 | Koshino |
| 5,888,223 A | | 3/1999 | Bray, Jr. |
| 6,008,433 A | | 12/1999 | Stone |
| 6,030,389 A | | 2/2000 | Wagner et al. |
| 6,086,593 A | * | 7/2000 | Bonutti ............... A61B 17/8004 128/898 |
| 6,099,531 A | * | 8/2000 | Bonutti ................ A61B 17/562 606/87 |
| 6,203,546 B1 | | 3/2001 | MacMahon |
| 6,235,059 B1 | | 5/2001 | Benezech et al. |

(Continued)

FOREIGN PATENT DOCUMENTS

DE WO2011082343 7/2011

OTHER PUBLICATIONS

"Femoral Opening Wedge Osteotomy System—Surgical Technique—Opening Wedge Osteotomy", LT0117A, 2008, Arthrex Inc.

(Continued)

*Primary Examiner* — David Bates
(74) *Attorney, Agent, or Firm* — Duane Morris LLP

(57) ABSTRACT

A bone re-angling device may be used in performing an osteotomy. The re-angling device may be a generally wedge-shaped body. The re-angling device maybe coupled to the bone using a fixation member.

8 Claims, 8 Drawing Sheets

(56) References Cited

U.S. PATENT DOCUMENTS

| | | |
|---|---|---|
| 6,432,106 B1 | 8/2002 | Fraser |
| 6,544,266 B1 | 4/2003 | Roger et al. |
| 6,635,087 B2 | 10/2003 | Angelucci et al. |
| 6,823,871 B2 | 11/2004 | Schmieding |
| 7,108,697 B2 | 9/2006 | Mingozzi et al. |
| 7,594,931 B2 | 9/2009 | Louis et al. |
| 7,744,630 B2 | 6/2010 | Lancial |
| 7,935,119 B2 | 5/2011 | Ammann |
| 7,976,566 B2 | 7/2011 | Michelson |
| 8,241,293 B2 | 8/2012 | Stone et al. |
| 8,784,457 B2 | 7/2014 | Graham |
| 8,828,087 B2 | 9/2014 | Stone et al. |
| 2002/0120335 A1 | 8/2002 | Angelucci et al. |
| 2004/0193269 A1 | 9/2004 | Fraser et al. |
| 2007/0198016 A1* | 8/2007 | Zang .............. A61B 17/80 606/86 A |
| 2007/0239278 A1 | 10/2007 | Heinz |
| 2008/0058822 A1 | 3/2008 | Bonutti |
| 2008/0108997 A1 | 5/2008 | Berrevoets et al. |
| 2008/0147073 A1* | 6/2008 | Ammann .............. A61B 17/15 606/87 |
| 2009/0043308 A1* | 2/2009 | Horacek ............ A61B 17/8095 606/87 |
| 2009/0082770 A1 | 3/2009 | Worner et al. |
| 2009/0177203 A1 | 7/2009 | Reiley |
| 2009/0264935 A1 | 10/2009 | Imbert |
| 2010/0152782 A1 | 6/2010 | Stone et al. |
| 2011/0087295 A1 | 4/2011 | Kubiak et al. |
| 2011/0213376 A1 | 9/2011 | Maxson et al. |
| 2012/0130501 A1 | 5/2012 | Cachia |
| 2012/0184959 A1 | 7/2012 | Price et al. |
| 2012/0191211 A1 | 7/2012 | Drozd |
| 2012/0232596 A1 | 9/2012 | Ribeiro |

OTHER PUBLICATIONS

"OSferion—The Next Generation in β-TCP Bone Void Fillers with the Highest Load Resistance Yet", LB0113A, 2007, Arthrex Inc.

Tanaka, T., et al., "Bone Formation and Bioresorption After Implantation of Beta-Tricalcium Phosphate Blocks with 60% and 75% Porosity in Opening-Wedge High Tibial Osteotomy", 53rd Annual Meeting of the Orthopaedic Research Society, Poster No. 1606.

Walsh, WR, et al., "Healing of a Critical Size Defect in Sheep Using Bone Graft Substitutes in Block Form", 53rd Annual Meeting of the Orthopaedic Research Society, Poster No. 1433.

Auld, J., et al., "In Vivo Evaluation of β-TCP Bone Graft Substitutes in a Bilateral Tibial Defect Model", 52nd Annual Meeting of the Orthopaedic Research Society, Paper No. 1712.

Ogose, Akira, et al., "Histological Examination of β-Tricalcium Phosphate Graft in Human Femur" J Biomed Mater Res (Appl Biomater), 2002, 601-604, vol. 63, Wiley Periodicals, Inc.

Ogose, Akira, et al., "Histological Assessment in Grafts of Highly Purified Beta-Tricalcium Phosphate (OSferion®) in Human Bones", Biomaterials, 2006, 1542-1549, vol. 27, Science Direct.

"BIOFOAM® Wedge System", FA022-109, 2010, Wright Medical Technology, Inc.

"BIOFOAM® Wedge System", FA724-1208, 2010, Wright Medical Technology, Inc.

"DARCO® MRS™—Locked Plating System for Reconstructive Rearfoot Surgery", SO118-407, 2008, Wright Medical Technology, Inc.

"TomoFix™ Osteotomy System with chronOS™ Option Technique Guide", J5606-B, 2005, Synthes (USA).

Lamping, Jeffrey William, "The Development of Goat Models to Evaluate the Effectiveness of Negative Pressure in Promoting Tissue Ingrowth into Porous Metal Implants", Submitted to the Graduate Degree Program in Bioengineering and the Graduate Faculty of the University of Kansas in partial fulfillment of the requirements for the degree of Master of Science, Defended Apr. 12, 2012.

* cited by examiner

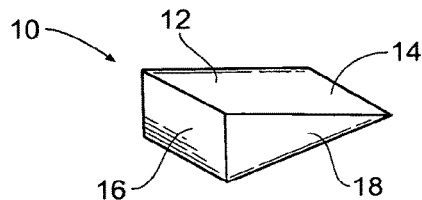
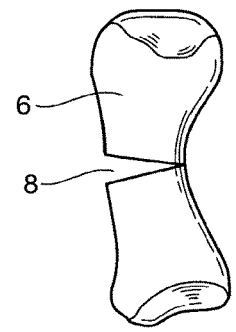
Fig. 3
Fig. 4A
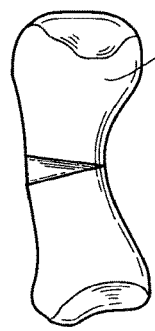
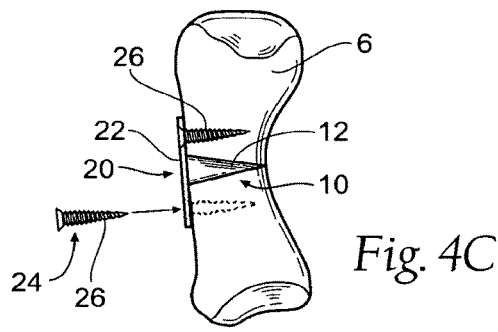
Fig. 4B
Fig. 4C
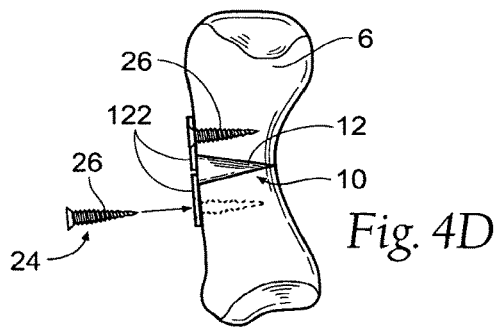
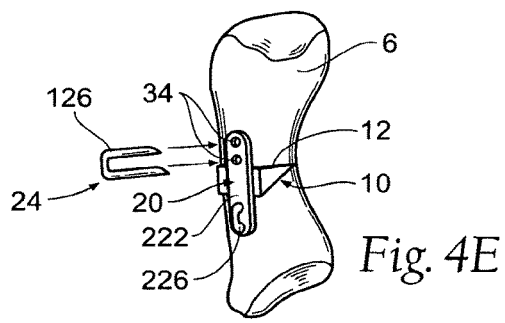
Fig. 4D
Fig. 4E
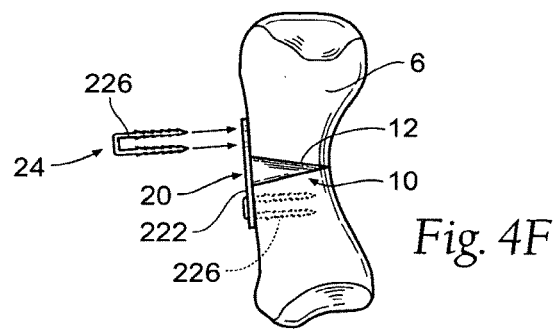
Fig. 4F

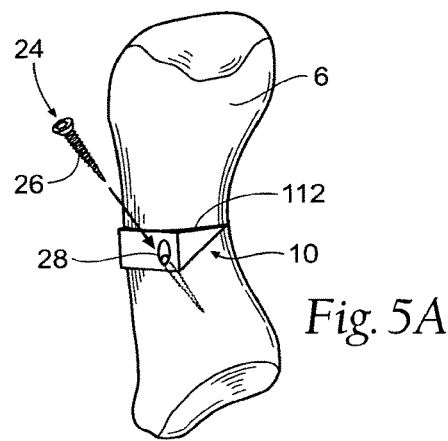
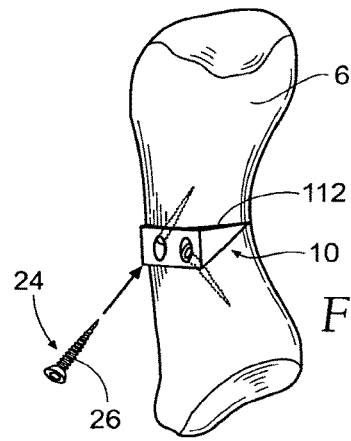
Fig. 5A
Fig. 5B
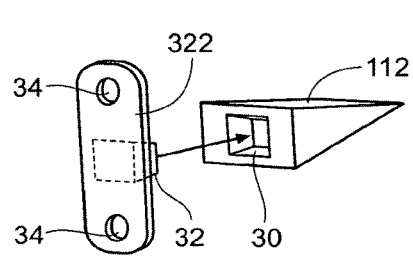
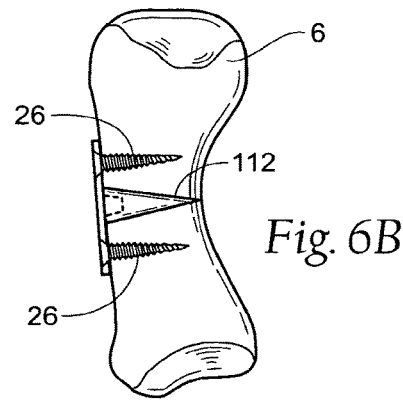
Fig. 6A
Fig. 6B
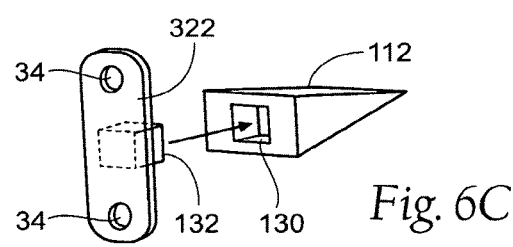
Fig. 6C

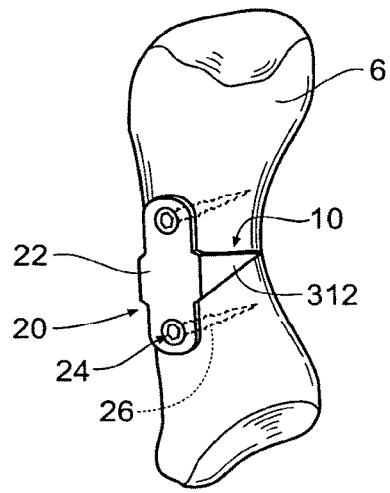
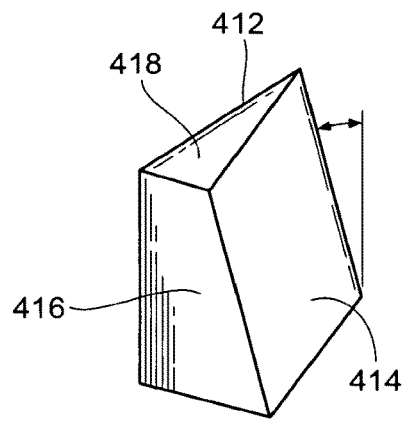
Fig. 8  Fig. 9A
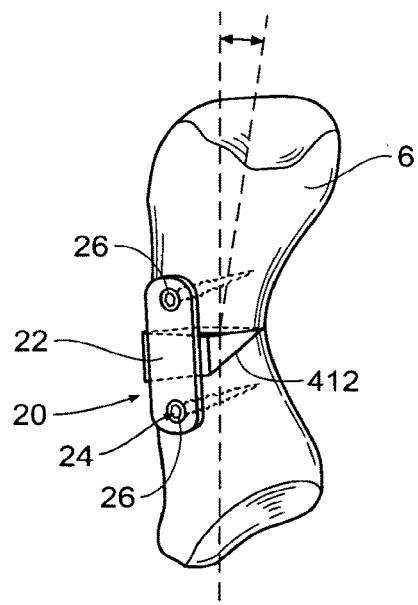
Fig. 9B

DEVICES, SYSTEMS AND METHODS FOR RE-ALIGNMENT OF BONE

CROSS-REFERENCE TO RELATED APPLICATIONS

This application is a continuation of U.S. patent application Ser. No. 13/747,031, filed Jan. 22, 2013, which was a division of U.S. patent application Ser. No. 12/006,720, filed Jan. 4, 2008, the entirety of each of which is herein incorporated by reference.

FIELD OF THE INVENTION

The invention generally relates to devices, systems, and methods for realignment of bone, e.g. during bony osteotomy.

BACKGROUND OF THE INVENTION

There are many occasions in orthopedic surgery when a bone is angled improperly due to congenital deformity, trauma, failed surgeries, and uneven arthritic wear in joints. A surgical operation called an osteotomy is done to correct this misalignment. In an osteotomy the bone is cut and then realigned to correct the improper angle.

In an osteotomy procedure, the surgeon removes a wedge of bone near a damaged joint. The procedure shifts weight from an area where there is damaged cartilage to an area where there either more cartilage or healthier cartilage. In this manner, weight is spread more evenly across the joint cartilage.

Osteotomy is commonly performed on the knee or hip joint. Osteotomy may help correct knee deformities such as bowleg or knock-knee deformities. Osteotomy may also be used to correct damage due to arthritis. For example, osteotomy may be performed in patients too young for a total joint replacement.

It is desirable to provide a new device which both simplifies the re-angling operations and enables correction to be more precise.

SUMMARY OF THE INVENTION

The invention provides devices, systems, and methods for re-aligning or re-angling a bone.

One aspect of the invention provides a system comprising a body sized and shaped to re-align a bone region toward a desired anatomic position and at least one fixation member for securing the body to the bone region.

In one embodiment, the fixation member includes at least one fixation plate sized and configured for association with the body to secure the body to the bone region.

In one embodiment, the fixation member comprises at least one screw and/or at least one staple and/or at least one stem.

In one embodiment, the body includes at least one aperture formed through it sized and configured for engagement with a fixation member. In this arrangement, the aperture can include internal threads for receiving a screw.

In one embodiment, the body is generally wedge-shaped.

In one embodiment, the fixation member includes a fixation plate formed with a first surface geometry. In this arrangement, the body includes a second surface geometry that mates with the first surface geometry.

In one embodiment, the system further comprises a total joint replacement including a stem. In this arrangement, the body includes an aperture formed through it sized and configured for engaging the stem.

Another aspect of the invention provides an osteotomy device comprising a generally wedge-shaped body and at least one intramedullary post extending from the wedge-shaped body.

Another aspect of the invention provides a method comprising providing a body sized and shaped to re-align a bone region toward a desired anatomic position and at least one fixation member for securing the body to the bone region. The method includes selecting an bone region, forming a cavity in the bone region sized and configured to receive the body, and inserting the body in the bone region to re-aligned the bone region toward a desired anatomic position. The method includes fixing the body to the bone region with the fixation member.

Another aspect of the invention provides a method comprising providing a body sized and shaped to re-align a bone region toward a desired anatomic position and at least one fixation plate sized and configured for association with the body to secure the body to the bone region. The method includes selecting an bone region, forming a cavity in the bone region sized and configured to receive the body, and inserting the body in the bone region to re-aligned the bone region toward a desired anatomic position. The method includes fixing the body to the bone region with the fixation plate.

Another aspect of the invention provides a method comprising providing a body sized and shaped to re-align a bone region toward a desired anatomic position, the body including at least one aperture formed through it sized, and a fixation member sized and configured for engagement with aperture. The method includes selecting a bone region, forming a cavity in the bone region sized and configured to receive the body, and inserting the body in the bone region to re-align the bone region toward a desired anatomic position. The method includes fixing the body to the bone region by engaging the fixation member through the aperture.

Other objects, advantages, and embodiments of the invention are set forth in part in the description which follows, and in part, will be obvious from this description, or may be learned from the practice of the invention.

BRIEF DESCRIPTION OF THE DRAWINGS

FIG. 3 is a perspective view of a re-angling device according to the present invention.

FIG. 4A is a plan view of a bone with a wedge shaped gap cut therein.

FIG. 4B shows a re-angling device of the type shown in FIG. 3 being inserted into the bone of the type shown in FIG. 4A.

FIGS. 4C to 4F show a re-angling device of the type shown in FIG. 3 being secured to a bone of the type shown in FIG. 4A using alternative fixation plate and fixation member.

FIGS. 5A and 5B show an alternative embodiment of a re-angling device being inserted into a bone.

FIG. 6A is an exploded perspective view of an alternative re-angling device and fixation plate wherein the re-angling device is formed with a protrusion and the fixation plate is formed with a mating aperture.

FIG. 6B shows the alternative re-angling device and fixation plate of FIG. 6A secured in a bone of the type shown in FIG. 4A.

FIGS. 6C to 6F show additional alternative embodiments of the re-angling device and fixation plate of FIG. 6A.

FIG. 8 shows an alternative re-angling device with a integrally formed fixation plate secured in a bone of the same type as shown in FIG. 4A.

FIG. 9A is a perspective view of an alternative embodiment of a re-angling device.

FIG. 9B shows the alternative re-angling device of FIG. 9A secured to a bone of the same type as shown in FIG. 4A by a fixation plate and fixation members.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
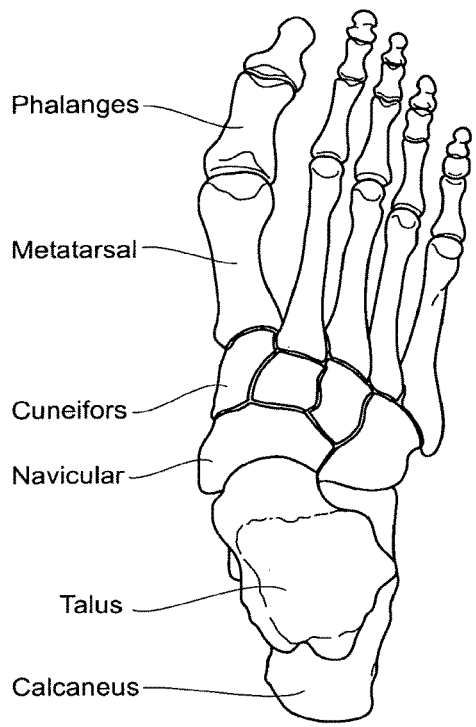
FIG. 1 is a top view of a foot.
Figure 2:
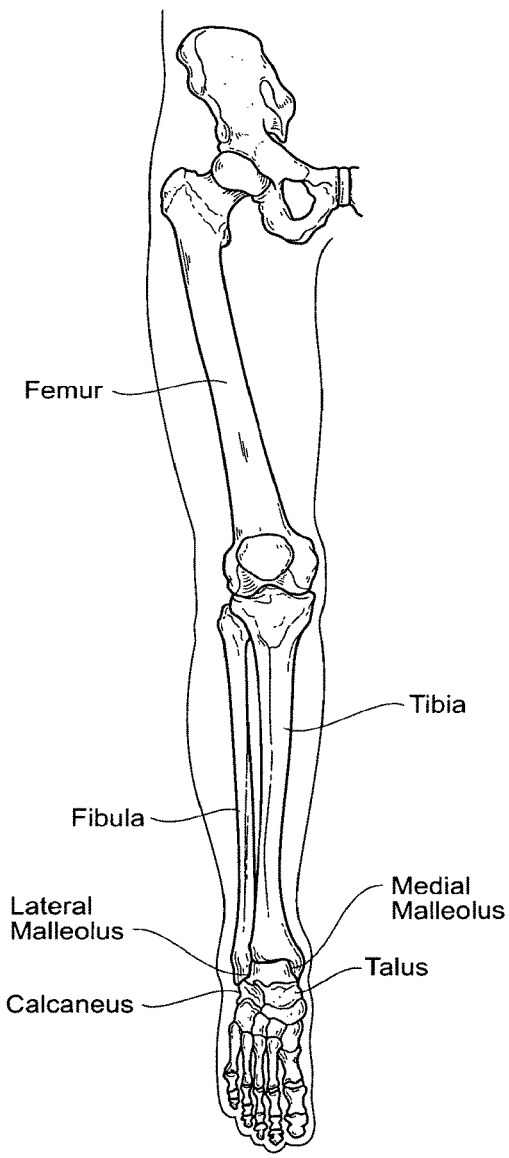
FIG. 2 is a front view of a leg.

FIGS. 1 and 2 show the anatomy of the human foot and leg, respectively. While it is contemplated that osteotomy may be in any part of the human anatomy, osteotomy is commonly performed on the metatarsal and the femur.

I. Re-Angling Device with Separate Fixation Plate

FIG. 3 shows a device 10 for re-angling or realigning a bone region according to the present invention. This device 10 is sized and configured to be inserted into a gap formed in the bone region to accommodate placement of the device 10. The device 10 is sized and configured to re-angle or realign the bone region toward a desired anatomic position, e.g., during an osteotomy procedure.

In a first illustrated embodiment, the re-angling device 12 is generally wedge shaped, and is sized and configured to fit into a wedge-shaped gap cut into the bone region. The size and configuration of the re-angling device 12 can vary, as long as it functionally serves to re-angle or realign the bone region in a desired manner.

In the embodiment shown in FIG. 3, the re-angling device 12 includes a generally rectangular base 16, a pair of wedge surfaces 14 which extend from laterally opposed edges of the base 16 and meet at a point opposite the base 16, and a pair of end surfaces 18 which extend from laterally opposed edges of the base 16 and engage one edge of each wedge surface 14.

In order to insert the device 12 into the bone 6, an appropriately sized wedge of bone is removed from the application site, creating a wedge-shaped gap 8, as shown in FIG. 4A. The application site is chosen by the physician based on the anatomy of the patient. The gap 8 is created using any appropriate surgical device, such as an appropriately sized and configured surgical saw. The device 12 is then inserted into the gap 8 in the bone 6 as shown in FIG. 4B. The device 12 may then be secured to the bone 6. The device 12 may be secured to the bone by any known method used in the art, for example, and not limited to bone cement, a temporary plate, and a permanent plate.

In one method of fixation, as shown in FIG. 4C, the device 12 is secured in the gap by placing a fixation plate 20 over the re-angling device 12. The fixation plate 20 is then attached to the bone 6 using a fixation member 24. In some circumstances, it may be desirable to drill pilot holes in either the fixation plate 20 or the bone 6 prior to inserting the fixation member 24. The fixation member 24 preferably extends through the fixation plate 20 and into the bone 6 to secure the re-angling device 12 to the bone 6.

In the embodiment shown in FIG. 4C, the fixation plate 20 takes the form of a single fixation plate 22 that extends across the entire length of the re-angling device 12.

It is also contemplated that the fixation plate 20 could take the form of multiple fixation plates 122, each of which extends across only a portion of the re-angling device, as shown in FIG. 4D.

In the representative embodiments shown in FIGS. 4C and 4D the fixation members 24 comprises screws 26, such as surgical screws. However, it should be understood that the fixation members may be chosen from a variety of fixation members known in the art. For example, the fixation member 24 could also be a bone staple 126, as shown in FIG. 4E or a barbed bone staple 226 as shown in FIG. 4F.

As shown in FIG. 4E, it may be desirable to provide the fixation plate 20 with at least one preformed aperture 34 through which a fixation member 24 may extend to secure the fixation plate 20 to the bone 6. The aperture 34 may be threaded or not threaded depending on the type of fixation member 24 to be used.

The size and shape of the device 10, fixation plate 20, and fixation members 24 are chosen by the physician based on each individual patient's anatomy and the type of bone in which the device is to be used.

The device 10, the fixation plate 20, and the fixation members 24 may be made of various materials commonly used in the prosthetic arts including, but not limited to, metals, ceramics, tantalum, polyethylene, biologic type polymers, hydroxyapetite, rubber, titanium, titanium alloys, tantalum, chrome cobalt, surgical steel, or any other total joint replacement metal and/or ceramic, bony in-growth surface, sintered glass, artificial bone, any porous metal coat, metal meshes and trabeculations, metal screens, uncemented metal or ceramic surface, other bio-compatible materials, or any combination thereof.

It may be desirable to provide the device 10, the fixation plate 20, and the fixation members 24 with surfaces, or a portion of a surface, that allow for bony ingrowth. The surfaces of the device 10, fixation plate 20, and fixation members 24 could be covered with biological bone substitute or biological stimulators for example, but not limited to hydroxygretite, calcium phosphate, calcium sulfate, or one of the bone morphogenic stimulators. Alternatively, the surfaces of device 10, the fixation plate 20, and the fixation members 24 could be covered with surface texturing to induce bony in-growth. The surface texturing can comprise, e.g., through holes, and/or various surface patterns, and/or various surface textures, and/or pores, or combinations thereof. The device 10 can be coated or wrapped or surfaced treated to provide the surface texturing, or it can be formed from a material that itself inherently possesses a surface conducing to bony in-growth, such as a porous mesh, hydroxyapetite, or other porous surface.

It may further be desirably for the device 10 to be covered with various coatings such as antimicrobial, antithrombogenic, and osteoinductive agents, or a combination thereof.

II. Re-Angling Device Fixed with One or More Crossing Screws

It is further contemplated that the re-angling device 10 described above may be fixed by one or more fixation members inserted through the alternative re-angling device 112 as shown in FIGS. 5A and 5B. The re-angling device 112 may take generally the same form as described above. However, in such an embodiment the need for a fixation plate 20 is eliminated.

In order to insert the alternative re-angling device 112 into the bone 6, an appropriately sized wedge of bone is removed from the application site, creating a wedge-shaped gap 8, as shown in FIG. 4A. The wedge-shaped gap 8 is formed using any appropriate surgical device, such as an appropriately sized and configured surgical saw. As discussed in reference to the embodiments above, the application site is chosen by the physician based on the anatomy of the patient. The size and particular configuration of the alternative re-angling device 112 is also selected by the physician based on the anatomy of the patient. The alternative re-angling device 112 may then be inserted into the gap 8 in the bone 6 and secured to the bone 8 by a fixation member 24 as shown in FIGS. 5A. In the illustrated embodiment the fixation member 24 comprises a threaded screw 26. The fixation member 24 is secured using any appropriate surgical devices, such as an appropriately sized and configured surgical screwdriver. As shown in FIG. 5A, the screw 26 is screwed though the re-angling device 112 and into the bone 6. It is further contemplated that multiple fixation members 24 could be utilized to fasten a single re-angling device 112, as shown in FIG. 5B. It may be desirable, but not necessary, to have a pilot hole in the re-angling device 112 to aid in insertion of the at least one fixation member 24. The re-angling device could be preformed with an aperture, such as a pilot hole 28, as shown in FIG. 5A. Alternatively, the pilot hole 28 could be drilled in the device 112 by the surgeon either before or after inserting the re-angling device 112 in the bone 6. The re-angling device 112 and fixation members 24 may be formed of any appropriate prosthetic material as describe above, and if desirable may include surfaces adapted to promote bony-in-growth as also described above.

III. Re-Angling Device with Slot for Attachment to a Fixation Plate

Figure 6D:
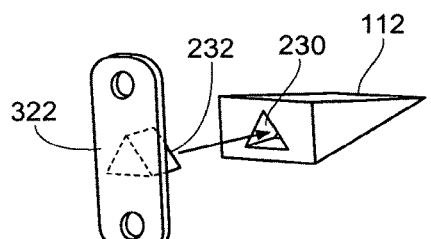

In an additional representative embodiment, a re-angling device 10 may be removably coupled to a fixation plate 20. As shown in FIG. 6A, the re-angling device 112 and fixation plate 322 may take generally the same form as described above. However, the re-angling device 112 includes a first surface geometry 30 and the fixation plate 20 includes a second surface geometry 32 that nests or mates with the first surface geometry 30. In the illustrated embodiment, the first surface geometry comprises a female aperture 30 and the second surface geometry comprises a mating male protrusion 32. The protrusion 32 is sized and configured to be received in the aperture 30 formed in the re-angling device 112. The mating male and female configurations may be reversed. That is, the first surface geometry on the device can comprise a male projection and the second surface geometry on the device comprises a mating female aperture.

Figure 6E:
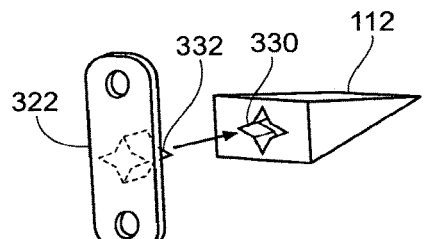
Figure 6F:
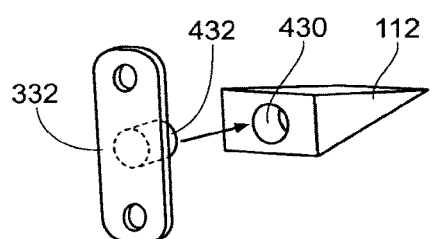
Figure 6G:
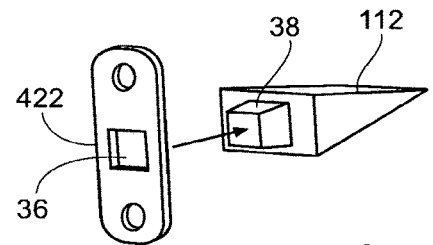
FIG. 6G is an exploded perspective view of an alternative re-angling device and fixation plate wherein the re-angling device is formed with an aperture and the fixation plate is formed with a mating protrusion.

In the first representative embodiment, the protrusion 32 and the aperture 30 each take a tapered rectangular shape. The protrusion 32 and aperture 30 may take any shape including, but not limited to square (see FIG. 6C), morse taper, triangular (see FIG. 6D), star-shaped (see FIG. 6E), or round (see FIG. 6F).

The re-angling device 112 and the fixation plate 322 may be coupled prior to inserting the re-angling device 112 into the bone 6. Alternatively, the re-angling device 112 may first be inserted into the bone 6, then the fixation plate 322 may be coupled to the re-angling device 112.

The fixation plate 322 is then fixed to the bone 6 by at least one fixation member 24, as shown in FIG. 6B and described in further detail above. In the illustrated embodiment, the fixation member 24 takes the form of a screw 26, however it should be understood that the fixation member 24 may take any form.

Alternatively the re-angling device 212 may be formed with a protrusion 38 and the fixation plate 422 may be formed with a mating aperture 36, as shown in FIG. 6H. The illustrated embodiment includes a rectangular tapered protrusion 38 and a generally rectangular aperture 36, however as described above, the aperture 36 and protrusion 38 may take any mating shape.

In order to insert the device 112 into the bone, an appropriately sized wedge of bone is removed from the application site, creating a wedge-shaped gap 8, as shown in FIG. 4A. The application site is chosen by the physician based on the anatomy of the patient.

The re-angling device 112,212, fixation plate 322,422 and fixation members 24 may be formed of any appropriate prosthetic material as describe above, and if desirable may include surfaces adapted to promote bony-in-growth as also described above.

IV. Re-Angling Device with Hole for Screw Attachment to a Fixation Plate

Figure 7A:
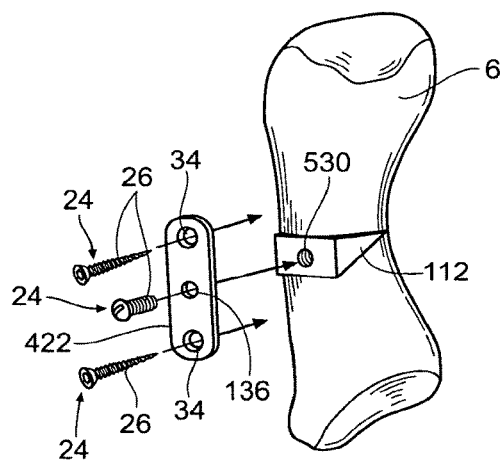
FIG. 7A is an exploded perspective view of a alternative re-angling device and fixation plate being inserted into a bone of the same type shown in FIG. 4A.
Figure 7B:
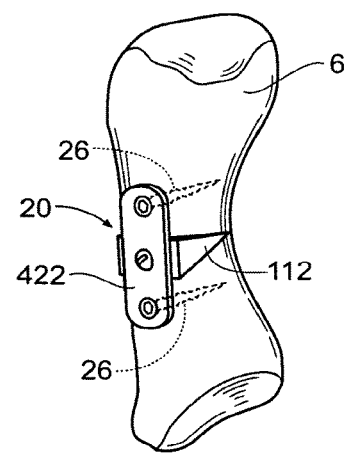
FIG. 7B shows the alternative re-angling device and fixation plate of FIG. 7A secured in a bone of the same type as shown in FIG. 4A.

In an additional representative embodiment both the re-angling device 10 and the fixation plate 20 may be preformed with an aperture. As shown in FIG. 7A, an aperture 530 is formed in the re-angling device 112 and an aperture 136 is formed in the fixation plate 422. In this manner, the fixation plate 422 may be fixed to the re-angling device 112 via a fixation member 24 such as a screw 26, as shown in FIG. 7B.

It is contemplated that the aperture 136 in the fixation plate 422 and the aperture 530 in the re-angling device 112 could be threaded as shown in FIG. 7A, or unthreaded. It is also contemplated that the aperture 136 in the fixation plate 422 could be threaded while the aperture 530 in the re-angling device 112 is not threaded, or vice versa.

It may be desirable, although not necessary, to provide the fixation plate 422 with at least one aperture 34 through which the fixation members 24 may extend as shown in FIG. 7A. It may be desirable, but not necessary, to provide the at least one aperture 34 with internal threads as shown in FIG. 7A.

The re-angling device 112 is generally wedge-shaped, as described above. The size and specific configuration of the re-angling device 112, fixation plate 422, and fixation members 24 are chosen by the physician based on each individual patient's anatomy and the type of bone in which the device 112 is to be used. The re-angling device 112 and the fixation plate 422 may be attached prior to inserting the re-angling device 112 into the bone 6, or after the re-angling device 112 has been inserted into the bone 6.

As described above with respect to the previous embodiments, in order to insert the re-angling device 112 into the bone 6, an appropriately sized wedge of bone is removed from the application site, creating a wedge-shaped gap 8, as shown in FIG. 4A. The wedge-shaped gap 8 is formed using any appropriate surgical device, such as an appropriately sized and configured surgical saw. As discussed in reference to the embodiments above, the application site is chosen by the physician based on the anatomy of the patient. The size and particular configuration of the re-angling device is also selected by the physician based on the anatomy of the patient. The re-angling device 112 is then inserted into the gap 8 in the bone 6 and secured to the bone 6 by a fixation member 24 as shown in FIGS. 7B. In the illustrated embodiment the fixation member 24 comprises a threaded screw 26, however it should be understood that any appropriate fastener may be utilized. The fixation member 24 is secured using any appropriate surgical devices, such as an appropriately sized and configured surgical screwdriver. As shown in FIG. 7B, the screw 26 is screwed though the fixation member 422 and into the bone 6.

The re-angling device 112, fixation plate 422 and fixation members 24 may be formed of any appropriate prosthetic material as describe above, and if desirable may include surfaces adapted to promote bony-in-growth as also described above.

V. Re-Angling Device with Integral Fixation Plate

In an additional representative embodiment, the re-angling device 10 and the fixation plate 20 are integrally formed as a single device 312, as shown in FIG. 8. The alternative re-angling device 312 may take generally the same wedge-shaped configuration as described above.

To insert the device 312 into the bone 6, an appropriately sized wedge of bone 6 is removed from the application site, creating a wedge-shaped gap 8, as shown above in FIG. 4A. The application site is chosen by the physician based on the anatomy of the patient. The device 312 is then inserted into the gap 8 in the bone as shown in FIG. 8 and secured to the bone 6. In one embodiment, the re-angling device 312 may be fixed to the bone through at least one fixation member 20. In the illustrated embodiment, the fixation member 20 takes the form of a screw 26. However, the fixation member 20 may comprise any suitable fixation member, including, by means of example a surgical screw or a surgical staple. As described above, and shown in FIG. 7A, it may be desirable, although not necessary to include apertures 34 in the fixation plate portion 22 of the device 312 through which the fixation members 24 may extend. It is further contemplated that in some situations it may be desirable, although not necessary, to provide the apertures 34 in the fixation plate portion 22 with preformed threads, as described in detail above.

The size and the particular configuration of the re-angling device 312 are preferably chosen by the physical based on the anatomy of the patient being treated.

The re-angling device 312 and fixation members 24 may be formed of any appropriate prosthetic material as describe above, and if desirable may include surfaces adapted to promote bony-in-growth as also described above.

VI. Wedge with Angle in Two Planes

In an additional representative embodiment shown in FIGS. 9A and 9B, the re-angling device 412 may be formed such that the bone 6 may be angled in two planes. The configuration of the re-angling device is similar to that shown in FIG. 3 and described above, however the base 416 is generally trapezoidal, rather than rectangular.

To insert the device 412 into the bone 6, an appropriately sized wedge of bone 6 is removed from the application site, creating a wedge-shaped gap 8, as shown above in FIG. 4A. The application site is chosen by the physician based on the anatomy of the patient. The device 412 is then inserted into the gap 8 in the bone as shown in FIG. 9B and secured to the bone 6. In one embodiment, the re-angling device 412 may be fixed to the bone through at least one fixation member 20. In the illustrated embodiment, the fixation member 20 takes the form of a screw 26. However, the fixation member 20 may comprise any suitable fixation member, including, by means of example a surgical screw or a surgical staple. As described above, and shown in FIG. 7A, it may be desirable, although not necessary to include apertures 34 in the fixation plate portion 22 of the device 312 through which the fixation members 24 may extend. It is further contemplated that in some situations it may be desirable, although not necessary, to provide the apertures 34 in the fixation plate portion 22 with preformed threads, as described in detail above.

The size and the particular configuration of the re-angling device 412 are preferably chosen by the physical based on the anatomy of the patient being treated.

The re-angling device and fixation members may be formed of any appropriate prosthetic material as describe above, and if desirable may include surfaces adapted to promote bony-in-growth as also described above.

VII. Re-Angling Device with Intramedullary Post

Figure 10A:
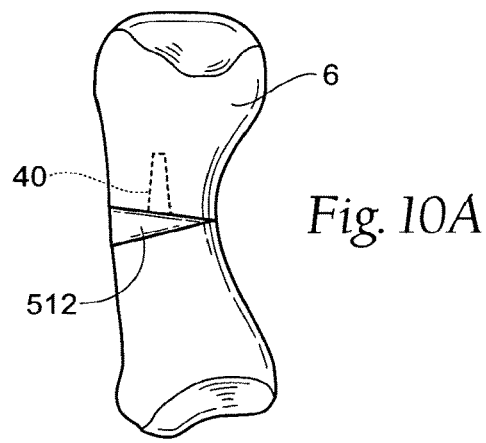
FIGS. 10A and 10B show an alternative re-angling device inserted into a bone of the type shown in FIG. 4A.

In an additional representative embodiment, the re-angling device 512 may include at least one intramedullary post 40, as shown in FIG. 10A. The intramedullary post 40 may extend into the bone 6 to further secure the re-angling device 512 within the bone 6.

To insert the device 512 into the bone 6, an appropriately sized wedge of bone 6 is removed from the application site, creating a wedge-shaped gap 8, as shown above in FIG. 4A. At least one aperture may be formed in the bone 6, the aperture being adapted to accept the at least one intramedullary post 40. The application site is chosen by the physician based on the anatomy of the patient. The device 512 is then inserted into the gap 8 in the bone as shown in FIG. 8 and secured to the bone 6. The size and the particular configuration of the re-angling device 512 are preferably chosen by the physical based on the anatomy of the patient being treated.

Figure 10B:
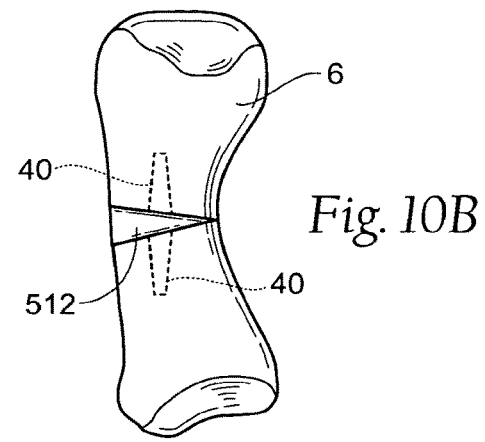

It is further contemplated that the re-angling device 512 could be formed with a pair of posts 40, as shown in FIG. 10B.

Figure 10C:
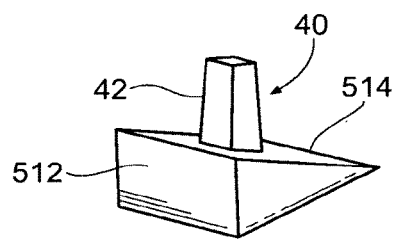
FIGS. 10C to 10G show various alternative embodiments of the re-angling device of FIG. 10A.
Figure 10D:
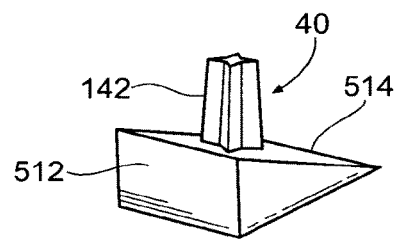
Figure 10E:
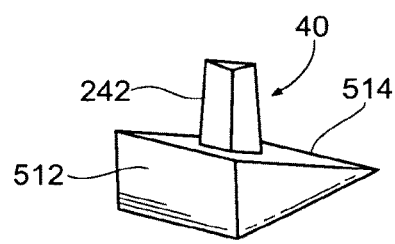
Figure 10F:
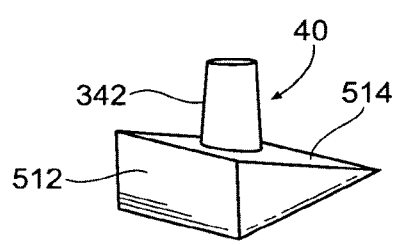
Figure 10G:
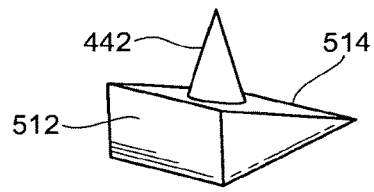
Figure 10H:
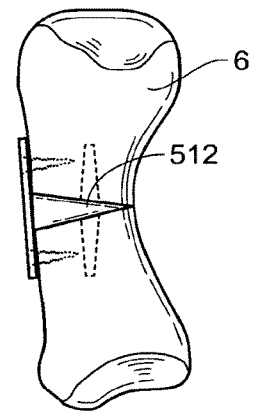
FIG. 10H shows the re-angling device of FIG. 10B secured in the bone with a fixation plate and fixation members.

It is further contemplated that the post 40 on the re-angling device 512 could take any shape. For example, the post could be square (see FIG. 10C), star-shaped (see FIG. 10D), triangular (see FIG. 10E), rounded (see FIG. 10F) or pointed (see FIG. 10G).

The re-angling device 512 may be formed of any appropriate prosthetic material as describe above, and if desirable may include surfaces adapted to promote bony-in-growth as also described above.

Figure 11A:
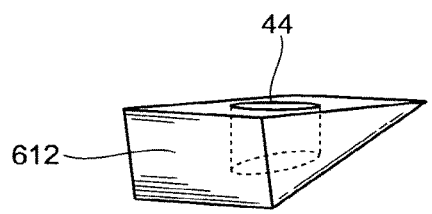
FIG. 11A is a perspective view of an alternative embodiment of the re-angling device of FIG. 3 with a hole therethrough for a total joint replacement stem.

VIII. Re-Angling Device for use with Stem of Total Joint Replacement or Internal Fixation It is also contemplated that any of the re-angling devices described above may be formed with a hole 44 therethrough as shown in FIG. 11A.

Figure 11B:
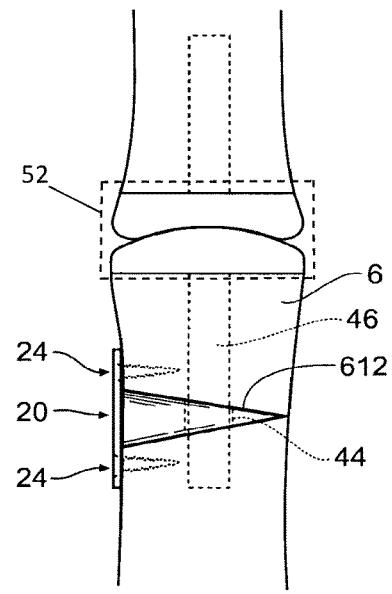
FIG. 11B shows the re-angling device of FIG. 11A inserted into a bone.
Figure 11C:
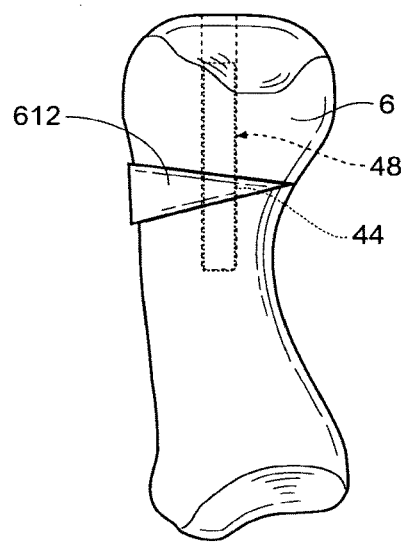
FIG. 11C is a perspective view of an alternative embodiment of the re-angling device like that shown in FIG. 11A, inserted into a bone with the hole receiving a fixation pin.
Figure 11D:
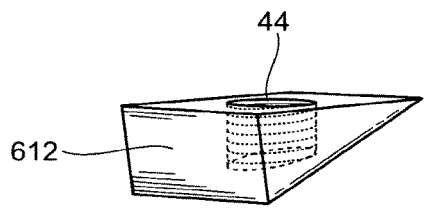
FIG. 11D is a perspective view of an alternative embodiment of the re-angling device like that shown in FIG. 11A, the hole being internally threaded for receiving a screw.
Figure 11E:
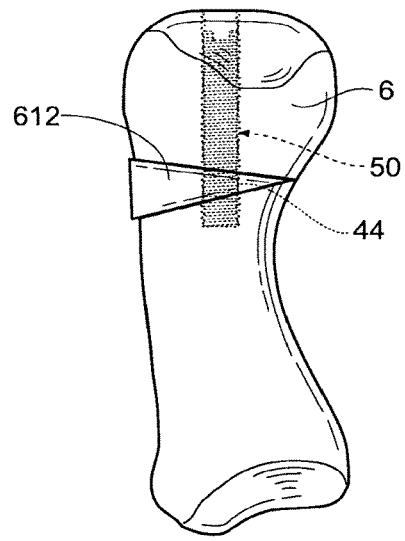
FIG. 11E shows the re-angling device of FIG. 11E inserted into a bone and fixated with a screw through the hole.

The hole 44 may be sized and configured for the particular application. For example, the hole 44 may be sized and configured such that when the re-angling device 612 is inserted into the bone 6, the stem 46 of a total joint replacement 52 may be inserted through the hole 44, as shown in FIG. 11B. Alternatively, the hole 44 may be sized and configured for receiving a pin 48, as shown in FIG. 11C. Alternatively, the hole 44 may be internally threaded, as shown in FIG. 11D, and be sized and configured for receiving a screw 50, as shown in FIGS. 11D and 11E. In any embodiment, the basic configuration of the re-angling device 612 is the same as described above. The particular size and configuration of the device 612 is determined by the physician based on the bone being treated and the anatomy of the patient.

In order to insert the device 612 into the bone, an application site is chosen by the physician based on the anatomy of the patient. An appropriately sized wedge of bone is removed from the application site, creating a wedge-shaped gap 8, as shown in FIG. 4A. The device 612 may then be inserted into the gap in the bone as shown in FIG. 11B. The device 612 may then be secured to the bone 6 by any known method used in the art. For example, the device 612 may be secured in the gap 8 by placing a fixation plate 20 over the re-angling device 612, as FIG. 11B shows. The fixation plate 20 can be attached to the bone 6 using at least one fixation member 24. The fixation member 24 preferably extends through the fixation plate 20 and into the bone 6 to secure the re-angling device 612 to the bone 6. In the illustrative embodiment, the fixation member 24 comprises at least one screw, however any appropriate fixation member 24 may be utilized without departing from the invention. In FIG. 11B, the re-angling device 612 is oriented so that the hole 44 receives the stem 46 of a total joint replacement 52. In other embodiments, the device 612 may be oriented so that the hole receives a pin 48 (FIG. 11C) or a screw 50 (FIG. 11E), which can be installed using standard surgical procedures known in the art. The pin 48 or screw 50 secures the re-angling device 612 to the bone through the hole 44. In these arrangements, a fixation plate 20 (as shown in FIG. 11B) need not be provided, but optionally, it can be, if additional fixation is desired.

It may be desirable to provide the fixation plate 20 or plates with at least one preformed aperture 34 through which a fixation member 24 may extend to secure the fixation plate 20 to the bone 6, as shown in FIGS. 6A and 6B. The aperture 34 may be threaded or not threaded.

The re-angling device 612 and fixation members 20, 24, 46, 48, and 50 may be formed of any appropriate prosthetic material as describe above, and if desirable may include surfaces adapted to promote bony-in-growth as also described above.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:
1. A method, comprising:
cutting a wedge-shaped gap in a bone between a first end of the bone and a second end of the bone;
drilling a hole into the bone such that the hole extends from the first end of the bone to the wedge-shaped gap in the bone;
inserting a body of a bone fixation system into the wedge-shaped gap to angle a section of the bone to a predetermined angle, the body including a first side, a second side, and a third side, the first and second sides disposed in an angled relationship to one another and the third side extending between the first and second sides, the body defining a channel extending inwardly from the first side; and
inserting an elongate member into the hole defined by the first end of the bone until the elongate member is received within the channel defined by the body to secure the body, wherein the elongate member is a stem of a total joint replacement system.

2. The method of claim 1, wherein the channel extends through the body from the first side to the second side.

3. The method of claim 2, wherein the elongate member is received within the channel such that the elongate member extends from the first side to the second side.

4. The method of claim 1, further comprising:
placing a fixation plate against bone adjacent to the third side of the body; and
securing the fixation plate to the bone using at least one fixation member.

5. The method of claim 4, wherein the at least one fixation member includes a screw.

6. A method, comprising:
cutting a wedge-shaped gap in a bone between a first end of the bone and a second end of the bone;
drilling a hole into the bone such that the hole extends from the first end of the bone to the wedge-shaped gap in the bone;
inserting a body of a bone fixation system into the wedge-shaped gap to angle a section of the bone to a predetermined angle, the body including a first side, a second side, and a third side, the first and second sides disposed in an angled relationship to one another and the third side extending between the first and second sides, the body defining a channel extending through the body from the first side to the second side; and
inserting an elongate member into the hole defined by the first end of the bone until the elongate member is received within the channel defined by the body to secure the body, wherein the elongate member is a stem of a total joint replacement system.

7. The method of claim 6, further comprising:
placing a fixation plate against bone adjacent to the third side of the body; and
securing the fixation plate to the bone using at least one fixation member.

8. The method of claim 7, wherein the at least one fixation member includes a screw.

* * * * *